US010603412B2

(12) United States Patent
Wong et al.

(10) Patent No.: US 10,603,412 B2
(45) Date of Patent: Mar. 31, 2020

(54) POLYMERIC BASED AND SURFACE TREATED METALLIC HYBRID MATERIALS AND FABRICATION METHODS THEREOF

(71) Applicants: VERSITECH LIMITED, Hong Kong (CN); City University of Hong Kong, Hong Kong (CN)

(72) Inventors: Hoi Man Karen Wong, Hong Kong (CN); Wai Kwok Kelvin Yeung, Hong Kong (CN); Man Chee Kenneth Cheung, Hong Kong (CN); Dip Kei Keith Luk, Hong Kong (CN); Kin On John Lam, Hong Kong (CN); Kim Ho Paul Chu, Hong Kong (CN)

(73) Assignees: Versitech Limited, Hong Kong (CN); City University of Hong Kong, Hong Kong (CN)

(*) Notice: Subject to any disclaimer, the term of this patent is extended or adjusted under 35 U.S.C. 154(b) by 0 days.

(21) Appl. No.: 16/119,633

(22) Filed: Aug. 31, 2018

(65) Prior Publication Data
US 2018/0369453 A1 Dec. 27, 2018

Related U.S. Application Data

(62) Division of application No. 12/836,326, filed on Jul. 14, 2010.
(Continued)

(51) Int. Cl.
*A61L 27/58* (2006.01)
*A61L 27/44* (2006.01)

(52) U.S. Cl.
CPC ............ *A61L 27/58* (2013.01); *A61L 27/446* (2013.01); *A61L 2400/18* (2013.01)

(58) Field of Classification Search
CPC ...... A61L 27/58; A61L 27/446; A61L 2400/18
See application file for complete search history.

(56) References Cited

U.S. PATENT DOCUMENTS

| 5,916,585 A | * | 6/1999 | Cook | ...................... A61L 27/34 |
| | | | | 424/426 |
| 2004/0034409 A1 | | 2/2004 | Heublein et al. | |

(Continued)

FOREIGN PATENT DOCUMENTS

EP 0050215 A1 4/1982
WO WO-2007/041972 A1 4/2007

OTHER PUBLICATIONS

Bruggeman et al. "Biodegradable xylitol-based elastomers: in vivo behavior and biocompatibility" J Biomed Mater Res A. Oct. 2010; 95(1):92-104) (Year: 2010).*

(Continued)

*Primary Examiner* — Jessica M Roswell
(74) *Attorney, Agent, or Firm* — Saliwanchik, Lloyd & Eisenschenk

(57) ABSTRACT

Novel hybrid materials and fabrication methods thereof are provided. The novel hybrid materials can include a biodegradable polymer and a biodegradable metallic material. The hybrid material can also include a coupling agent between the biodegradable metallic material and the biodegradable polymer. A method of fabricating a hybrid material can include performing a surface treatment process on the biodegradable metallic material, and then either performing a solvent formation method or a thermal formation method.

18 Claims, 3 Drawing Sheets

Related U.S. Application Data

(60) Provisional application No. 61/225,279, filed on Jul. 14, 2009.

(56) References Cited

U.S. PATENT DOCUMENTS

| | | |
|---|---|---|
| 2005/0137679 A1 | 6/2005 | Changelian et al. |
| 2006/0093771 A1 | 5/2006 | Rypacek et al. |
| 2006/0198869 A1 | 9/2006 | Furst et al. |
| 2006/0228389 A1 | 10/2006 | Li et al. |
| 2008/0069858 A1 | 3/2008 | Weber |
| 2008/0152929 A1 | 6/2008 | Zhao |
| 2008/0177378 A1 | 7/2008 | Asgari |
| 2008/0248086 A1 | 10/2008 | Asgari |
| 2008/0249637 A1 | 10/2008 | Asgari |
| 2008/0249638 A1 | 10/2008 | Asgari |
| 2009/0319032 A1 | 12/2009 | Weber et al. |

OTHER PUBLICATIONS

Office Action dated Jul. 9, 2015 in European Application No. 10799352.9.

Wong, H. et al., "A biodegradable polymer-based coating to control the performance of magnesium alloy orthopaedic implants," *Biomaterials*, 2010, 31:2084-2096, Elsevier Ltd.

Lin, J. et al., "Surface Modification of Inorganic Oxide Particles with Silane Coupling Agent and Organic Dyes," *Polymers for Advanced Technologies*, 2001, 12:285-292, John Wiley & Sons, Ltd.

Lu, T. et al., "Surface modification of biomaterials using plasma immersion ion implantation deposition," *Interface Focus*, Jun. 6, 2012, 2(3):325-336, The Royal Society.

Gupta, D., "Plasma Immersion Ion Implantation (PIII) Process-Physics and Technology," *International Journal of Advancements in Technology*, Oct. 2011, 2(4):471-490.

\* cited by examiner

POLYMERIC BASED AND SURFACE TREATED METALLIC HYBRID MATERIALS AND FABRICATION METHODS THEREOF

CROSS-REFERENCE TO RELATED APPLICATIONS

The subject application is a divisional application of U.S. application Ser. No. 12/836,326, filed Jul. 14, 2010, which claims the benefit of U.S. Provisional Application Ser. No. 61/225,279, filed Jul. 14, 2009, which are incorporated herein by reference in their entirety.

BACKGROUND OF THE INVENTION

Implants are used very often in surgical, orthopedic, dental, and other related applications, including tissue engineering. One important issue with implants is that due to biomechanical and physiologic requirements, an implant material should have a certain mechanical strength or elasticity to be incorporated into the target tissue and anatomic region. Also, degradability or possibly even incorporating pharmacologically or therapeutically active agents is also desirable.

Several different materials for implants have been used, including metal. Metallic implant materials are usually favorable in terms of toughness, ductility, and fatigue resistance. On the other hand, they are often stiffer than natural bone, resulting in stress shielding. The phenomenon of stress shielding is based on the effect that the implant material bears more of the mechanical load if it is stiffer than the surrounding tissue. This results in a "shielding" of the natural bone tissue from the mechanical load triggering the resorption processes of bone.

Patients with orthopedic fractures or deformities are sometimes treated with surgically implanted metallic materials. The most common metallic materials used in fracture fixation or total joint devices are medical-grade non-degradable metals, such as stainless steel, titanium, and cobalt-chromium-based alloys. Existing permanent metallic implants for fracture fixation and total hip replacement can often cause stress shielding effects due to the mismatch of the mechanical properties between these metallic implants and natural bone. That is, due to a mismatch of the mechanical properties between these metallic implants and natural bone, the major obstacle in using these non-degradable permanent metal implants is that they may cause stress shielding effects, thereby leading to bone loss around the implant. Patients who undergo orthopedic procedures such as fracture fixation, often undergo a second surgery after treatment is done in order to avoid this post-operative complication.

Polymeric implants are sometimes used as an alternative to metallic implants. However, existing polymeric implants often do not have appropriate mechanical strength to withstand load-bearing conditions.

Biodegradable metallic implants such as magnesium alloys have sometimes been used. However, in addition to a mismatch in mechanical properties and poor biocompatibility, magnesium alloys exhibit problems with a rapid degradation rate and hydrogen gas accumulation upon implantation. Rapid corrosion results in the release of a large amount of magnesium ions together with a large volume of hydrogen gas generated. As shown in Reactions (1)-(3) below, if an increase in corrosion rate leads to an increase in magnesium ions. Accordingly, magnesium hydroxide is formed, and hydrogen gas is generated. The human body itself is able to absorb a small amount of hydrogen gas.

An alloying modification method is sometimes applied to attempt to improve the corrosion resistance of magnesium alloys. Although alloying can improve the corrosion resistance of magnesium alloy, this technique may introduce biological toxicity due to the use of rare earth metals, such as cerium and yttrium. Additionally, the compatibility with living cells remains a problem. The mechanical properties of magnesium alloy are closer to human natural bone than those of other metallic materials such as titanium alloys and stainless steel. However, there is still a discrepancy between magnesium alloy and natural bone in terms of bulk mechanical properties.

$$H_2O \rightarrow H^+ + OH^- \quad \text{Reaction (1):}$$

$$2Mg \rightarrow Mg^{2+} + 2e^- \quad \text{Reaction (2):}$$

$$Mg + 2H_2O \rightarrow Mg(OH)_2 + H_2 \quad \text{Reaction (3):}$$

Each of the existing materials used for orthopedic implants exhibits potentially harmful problems. Thus, there exists a need in the art for an improved material that can be used as an implant in orthopedic and other medical applications, as well as in other non-medical applications where a durable substitute for traditional metals or plastics is desired.

BRIEF SUMMARY OF THE INVENTION

The present invention pertains to novel hybrid materials based on biodegradable polymers and surface-treated biodegradable metallic materials, as well as fabrication methods thereof. These novel hybrid materials are able to tackle the complications of conventional biodegradable materials (including magnesium-based materials), such as mismatched bulk mechanical properties, poor biocompatibility, rapid degradation, and hydrogen gas release upon degradation in orthopedic applications. In addition to the enhancement of biocompatibility, with the materials of the subjection invention, the degradation process can be manipulated by controlling the chemistry of polymeric materials and the surface treatment of metallic materials as well as their ratio when forming the hybrid materials. The novel materials and methods of the subject invention have several applications, including but not limited to orthopedic implantation.

In an embodiment, a hybrid material can comprise: a biodegradable polymer; a surface-treated biodegradable metallic material; and a silane coupling agent chemically bonded to the surface-treated biodegradable metallic material and the biodegradable polymer.

In another embodiment, a method of fabricating a hybrid material comprising a biodegradable polymer and a biodegradable metallic material can comprise: performing a surface treatment process on the biodegradable metallic material; dissolving the biodegradable polymer in an organic solvent to form a solution; adding the biodegradable metallic material, after the surface treatment process has been performed, to the solution; sonicating the solution; drying the solution to obtain a pre-hybrid material; and performing a heat treatment process on the pre-hybrid material.

Yet another embodiment is a method of fabricating a hybrid material comprising biodegradable polymer and a biodegradable metallic material, wherein the method can comprise: performing a surface treatment process on the biodegradable metallic material; melting a biodegradable polymer by a thermal process to obtain a polymer melt;

adding the biodegradable metallic material to the polymer melt to form a pre-hybrid material; shearing the pre-hybrid material in a first direction and a second direction; and compressing the pre-hybrid material along a third direction to obtain the hybrid material.

DETAILED DESCRIPTION OF THE INVENTION

The present invention pertains to novel hybrid materials including biodegradable polymers and surface-treated biodegradable metallic materials, as well as fabrication methods thereof. These novel hybrid materials are able to overcome the problems of conventional biodegradable materials (including magnesium-based materials), such as mismatched bulk mechanical properties, poor biocompatibility, rapid degradation, and hydrogen gas release upon degradation in orthopedic applications. In addition to the enhancement of biocompatibility, with the materials of the subjection invention, the degradation process can be manipulated by controlling the chemistry of polymeric materials and the surface treatment of metallic materials as well as their ratio when forming the hybrid materials. The novel materials and methods of the subject invention have several applications, including but not limited to orthopedic implantation. For example, the novel materials of the subject invention can be used for other medical applications, as well as for non-medical applications such as a substitute for metal and/or plastic in consumer goods.

Figure 1:
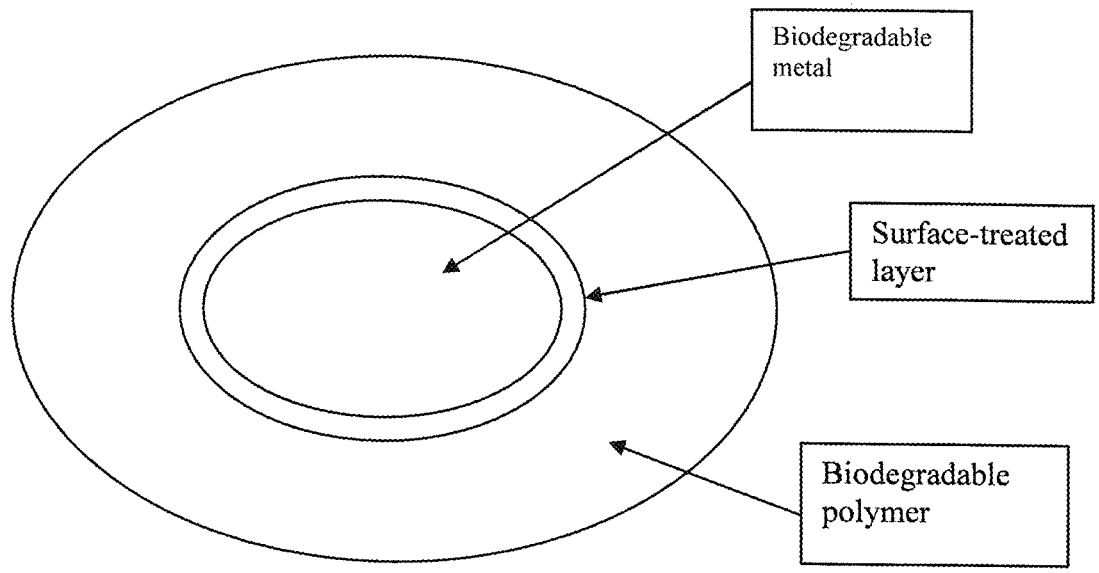
FIG. 1 shows a schematic representation of a unit of hybrid material according to an embodiment of the subject invention.

The hybrid materials of the subject invention, which can be used as biodegradable implants, can include polymeric and metallic materials. Referring to FIG. 1, the hybrid material can include a biodegradable metal with a surface treatment and a biodegradable polymer.

Biodegradable metallic implants can have an advantage over biodegradable polymeric implants since metal has better mechanical properties than polymers; this can be particularly advantageous in instances where the implants are used in a high load-bearing situation. Biodegradable metallic materials, such as magnesium alloys, are able to withstand higher mechanical loading than biodegradable polymeric materials. In an embodiment of the present invention, the biodegradable metallic material can include magnesium and/or a magnesium alloy. In another embodiment, the biodegradable metallic material can include iron and/or an iron alloy. In certain embodiments of the subject invention, the biodegradable metallic materials can be beads, rods, tubes, or any combination thereof.

With the hybrid materials of the subject invention, the mechanical properties of the materials can be modified so as to obtain the approximate mechanical properties of natural bones without inducing biological toxicity.

In addition, the subject invention provides novel methods of fabricating hybrid materials incorporating biodegradable polymers and surface-treated biodegradable metallic materials. The hybrid materials of the subject invention can achieve controllable degradation, controllable bulk mechanical properties similar to human bone, and superior biocompatibility to cells.

The hybrid materials of the subject invention can impart many advantageous benefits, including for patients undergoing orthopedic procedures. The subject invention can help eliminate the risks of having a metallic implant left inside the body, as well as the need for additional surgery for implant removal.

The biodegradable hybrid materials of the subject invention have many applications, including but not limited to, orthopedic implants for bone fracture fixation. For example, the hybrid materials can be used as different orthopedic implants including bone screws and bone plates. The hybrid materials can also be used in cardiovascular, dental, and/or renal procedures; and in innumerable non-medical applications where a durable substitute for metal or plastic is desired.

This subject invention involves new hybrid materials, and fabrication methods thereof, for a wide range of applications, including orthopedic, dental, and cardiovascular procedures. The novel fabrication methods can help control the material degradation process and provide bulk mechanical properties similar to natural bone. In addition, these new materials are highly compatible with cells, whereas related art degradable metallic materials are not.

The novel hybrid materials can be formed by biodegradable polymers and surface-treated biodegradable metallic materials. In a particular embodiment, the biodegradable metallic materials can include magnesium and/or magnesium alloys. In an embodiment, the biodegradable polymer can be derived from ε-caprolactone, either used alone or combined with other lactone monomers. The other lactone monomers, can include, for example, γ-butyrolactone (γ-BL), δ-valerolactone (δ-VL), γ-valerolactone (γ-VL), and γ-caprolactone (γ-CL). In further embodiments, other monomers can be used, for example, xylitol can be used to form a biodegradable xylitol-based polymer.

The biodegradable metallic materials can be surface-treated. In certain embodiments, the biodegradable metallic materials can be surface-treated by heat treatment, magnetron sputtering, plasma immersion ion implantation, or plasma immersion ion implantation and deposition before mixing with the polymer component.

In an embodiment of the present invention, the biodegradable polymer of the novel hybrid material can be a polymer or copolymer derived from ε-caprolactone. The polymer derived from ε-caprolactone (ε-CL) alone forms a biodegradable polymeric material referred to as polycaprolactone (PCL). Other biodegradable polymers can be formed by the copolymerization process using other lactone monomers such as γ-butyrolactone (γ-BL), δ-valerolactone (δ-VL), γ-valerolactone (γ-VL), and γ-caprolactone (γ-CL). The biodegradable polymer can be a polymer or copolymer of any of these monomers or any combination thereof. The formation process of the polymer can be either with or without catalysts. In an alternative embodiment, instead of chemically synthesizing the polymer from monomers, the polymer may be obtained by purchasing a commercially available sample. For example, granules of PCL with different molecular weights (for example 80,000 g/mol) are commercially available.

In a further exemplary embodiment, xylitol can be used to form a biodegradable xylitol-based polymer. For example, a biodegradable xylitol-based polymer can be formed by polycondensation of xylitol with water-soluble citric acid. In yet a further embodiment, other monomers can be used to form a biodegradable polymer.

In certain embodiments, the polymer used can be PCL, a biodegradable xylitol-based polymer, or a copolymer of ε-CL with one or more of γ-BL, δ-VL, γ-VL, and γ-CL.

In an embodiment of a fabrication process, after preparing the biodegradable polymer, the biodegradable metallic material can be surface-treated. There can be more than one biodegradable metallic material, and these materials can be in different forms. The biodegradable metallic material or materials is/are subjected to a surface modification process to change the surface chemistry for hybrid material formation. The modification method can be, for example, plasma immersion ion implantation or thermal treatment.

In certain embodiments, the modification method can be plasma immersion ion implantation with different sources such as aluminum, iron, silicon, strontium, calcium, zirconium, carbon, nitrogen, ammonia, and/or oxygen. In a further embodiment, the modification method can be thermal treatment. Depending on the biodegradable metallic material(s) used, the thermal treatment can allow formation of an oxide layer on the metallic surface. In yet a further embodiment, both plasma immersion ion implantation and thermal treatment can be performed. A change in surface chemistry can enhance the bonding or adhesion between the biodegradable metallic material(s) and a biodegradable polymeric substrate.

In an embodiment, coupling agents can be applied to help form chemical bonds between the polymer(s) and the metal(s). The coupling agent can be chemically bonded to a polymer and a metallic material of the hybrid material. The coupling agent can be, for example, a silane coupling agent. In certain embodiments, the coupling agent can be 3-(trimethoxysilyl)propylmethacrylate or 3-aminopropyltrimethoxysilane. A coupling agent treatment can be performed, optionally including a solvent and a catalyst. A catalyst can be, for example, propylamine or triethylamine; and a solvent can be, for example, cyclohexane or toluene.

After surface treatment, solvent formation and/or thermal formation can be performed to fabricate the hybrid materials. In an embodiment with solvent formation, the polymer(s) can be dissolved in a solvent. The solvent can be, for example, an organic solvent, such as a solvent wherein a ratio of weight of PCL/volume of dichloromethane (DCM) is about 1 g/ml, a solvent wherein a ratio of weight of PCL/volume of chloroform is about 1 g/ml, or a combination thereof. Note that, even though 1 g/ml DCM and 1 g/ml chloroform have been listed by way of example, embodiments of the subject invention are not limited thereto. Any reasonable concentration of organic solvent can be used. For example, an organic solvent wherein a ratio of weight of polymer/volume of solvent can be from about 0.05 g/ml to about 2.0 g/ml, or even greater, being limited only by the solubility of a chosen polymer in a chosen solvent as would be readily recognized by one of ordinary skill in the art.

In an embodiment, the biodegradable metallic material(s) can be thermally treated. Depending on the material(s), the thermal treatment can help establish an oxide layer on the metallic surface. Varying the proportions of thermally treated metallic material(s) to be mixed with the polymer solution can result in hybrid materials of varying concentrations. The metallic materials are preferable nano-sized or micro-sized units, such as beads, cones, rods, etc. The solution mixture can then be sonicated so that the metallic material(s) can be aligned or dispersed evenly within the polymer substrate. Next, the mixture can undergo a drying process. In certain embodiments, a second thermal treatment process can be performed on the hybrid materials to enhance the mechanical properties of the materials.

In certain embodiments, the biodegradable metallic material can be magnesium beads. The beads can have sizes of, for example, about 100 nm, about 45 μm, or about 150 μm, and can be thermally treated to help establish an oxide layer on the surface. In a specific embodiment, the thermal treatment can be performed at a temperature of about 100° C. for a period of time of about 60 minutes. Varying the proportions of thermally treated magnesium beads to be mixed with the polymer solution can result in hybrid materials of varying concentrations. The solution mixture can then be sonicated so that the beads can be aligned or dispersed evenly within the polymer substrate. Next, the mixture can undergo a drying process. In certain embodiments, a second thermal treatment process can be performed on the hybrid materials to enhance the mechanical properties of the materials.

The degradation rates and mechanical properties of the hybrid materials of the subject invention can be determined by the concentrations and reaction parameters during a fabrication method of the present invention.

The novel hybrid materials of the subject invention provide a stable degradation rate for the whole material since the polymer and metallic material are distributed approximately evenly. Additionally, strong bonds (e.g., chemical bonds) can form between the metallic material and the polymer. For example, a coupling agent can be used to modify the metallic material so that chemical bond can be formed with the polymer, thereby improving the mechanical properties of the hybrid material.

EXAMPLES

Example 1: Plasma Immersion Ion Implantation (PIII)

One of the surface modification methods can be PIII, and the implantation sources that can be used include nitrogen ($N_2$), oxygen ($O_2$), carbon (C), ammonia ($NH_3$), aluminum (Al), zirconium (Zr), iron (Fe), silicon (Si), strontium (Sr), calcium (Ca), and water. Table 1 shows implantation conditions for the implantation sources of nitrogen, water, and strontium. All values listed will work with slight variations, such that each value should be interpreted as having the word "about" in front of it.

TABLE 1

Implantation conditions for PIII for selected implantation sources

| Parameters | Sources | | |
| --- | --- | --- | --- |
| | Nitrogen ($N_2$) | Water ($H_2O$) | Strontium (Sr) |
| Base Pressure | $7.0 \times 10^{-6}$ Torr | $7.0 \times 10^{-6}$ Torr | $7.0 \times 10^{-6}$ Torr |
| Working Voltage | 40 kV | 40 kV | 15 kV |
| Pulse Width | 30 μs | 30 μs | 30 μs |
| Implantation Time | 4 hrs | 4 hrs | 3 hrs |
| Frequency | 200 Hz | 200 Hz | 200 Hz |
| Working Pressure | $5.0 \times 10^{-4}$ Torr | $6.0 \times 10^{-4}$ Torr | $6.4 \times 10^{-4}$ Torr |

Example 2: Plasma Immersion Ion Implantation and Deposition (PIII & D)

Apart from PIII, PIII together with deposition can be used as another surface treatment technique. Similar to PIII, different sources such as nitrogen ($N_2$), oxygen ($O_2$), carbon (C), ammonia ($NH_3$), aluminum (Al), zirconium (Zr), iron (Fe), silicon (Si), strontium (Sr), calcium (Ca), and/or water can be used for PIII & D. Table 2 shows the working parameters for implanting and depositing Al and $O_2$ at the same time. All values listed will work with slight variations, such that each value could be interpreted as having the word "about" in front of it.

TABLE 2

Implantation and deposition conditions for implanting and depositing Al and $O_2$ to form $Al_2O_3$

| Negative High Voltage Power Supply | |
| --- | --- |
| NH Current | 1.0 mA |
| NH Voltage | 15 kV |
| Pulse Duration | 300 μs |
| Frequency | 10 Hz |
| Pulsed Filtered Cathodic Arc Source | |
| Arc Current | 0.1 A |
| Arc Voltage | 92 V |
| Triggering Voltage | 12.6 kV |
| Coil Current | 2.3 A |
| Pulse Duration | 250 μs |
| Frequency | 10 Hz |
| Oxygen Flow | 10 sccm |

Example 3: Magnetron Sputtering

Magnetron sputtering can be used for a surface treatment process according to an embodiment of the subject invention. The sputtering source can be, for example, aluminum oxide ($Al_2O_3$). Tables 3 shows the process conditions during the magnetron sputtering process. All values listed will work with slight variations, such that each value could be interpreted as having the word "about" in front of it.

TABLE 3

Process conditions of magnetron sputtering

| Frequency | 40 kHz-60 kHz |
| --- | --- |
| Voltage | 100-1000 V |
| Current | 0.1-1 A |

Example 4: Thermal Treatment

Thermal treatment can be used for a surface modification method to induce an oxide layer formation. Table 4 shows an example of process conditions during thermal treatment. All values listed will work with slight variations, such that each value should be interpreted as having the word "about" in front of it.

TABLE 4

Thermal treatment process conditions

| Temperature | 60° C.-100° C. |
| --- | --- |
| Pressure | 100 mBar |
| Humidity | 10%-20% |
| Treatment Time | 8-24 hrs |

Example 5: Coupling Agent Treatment

A coupling agent treatment can be applied to the biodegradable metallic materials directly or after a surface treatment such as discussed and exemplified in any of Examples 1-3. Coupling agents can be silane coupling agents, such as 3-(trimethoxysilyl)propylmethacrylate and 3-aminopropyltrimethoxysilane ("ASCA"). The coupling agents can modify the surface of the biodegradable metallic materials. The coupling agent can be added to a solvent together with a catalyst. The treated or untreated biodegradable metallic materials can be added to the solution mixture which is then heated under reflux with nitrogen for a period of time at a given temperature. After the silane treatment, the metallic materials can be heat treated again in a low vacuum oven at a given temperature. Tables 5 and 6 show examples of coupling agent treatment process conditions using 3-(trimethoxysilyl)propylmethacrylate and 3-aminopropyltrimethoxysilane as the coupling agent, respectively. All values listed will work with slight variations, such that each value should be interpreted as having the word "about" in front of it.

TABLE 5

Process conditions with 3-(trimethoxysilyl)propylmethacrylate

| Silane Treatment | |
| --- | --- |
| Silane coupling agent | 3-(Trimethoxysilyl)propylmethacrylate (Weight of Mg/Volume of ASCA: 1 g/ml-20 g/ml) |
| Solvent | Cyclohexane |
| Catalyst | Propylamine |
| Treatment Temperature | 60° C.-80° C. |
| Treatment Time | 1-5 hrs |
| Post Heat Treatment | |
| Temperature | 80° C.-100° C. |
| Duration | 5-8 hrs |
| Pressure | 100 mBar |

TABLE 6

Process conditions with 3-aminopropyltrimethoxysilane

| Silane Treatment | |
| --- | --- |
| Silane coupling agent | 3-Aminoproyltrimethylsilane (Weight of Mg/Volume of ASCA: 1 g/ml-20 g/ml) |
| Solvent | Cyclohexane/Toluene |
| Catalyst | Triethylamine |
| Treatment Temperature | 60° C.-80° C./80° C.-110° C. |
| Treatment Time | 1-5 hrs |
| Post Heat Treatment | |
| Temperature | 80° C.-100° C. |
| Duration | 5-8 hrs |
| Pressure | 100 mBar |

Example 6: Solvent Formation Method

After surface treatment of the biodegradable metallic materials, the hybrid material can be fabricated by, for example, the solvent formation method. A solvent, e.g. an organic solvent such as DCM or trichloromethane (TCM; also known as chloroform) is used to dissolve the organic polymer (e.g., PCL). When the polymer is dissolved, the surface-treated biodegradable metallic materials (e.g., magnesium beads) are then added to the polymer solution. The mixture is then sonicated to let the metallic materials align or distribute evenly in the solution within the polymer substrate. After the process of sonication, the mixture is then dried. A heat treatment process is finally conducted to enhance the bonding and adhesion between the biodegradable metallic materials and the biodegradable polymer. The ratio of the polymer to the metallic materials can be varied. For example, 50%-99.9% polymer can be used, and 50%-0.1% metallic materials can be used. Table 7 shows an example of process conditions for solvent formation using PCL and magnesium beads. All values listed will work with slight variations, such that each value should be interpreted as having the word "about" in front of it.

TABLE 7

Process conditions for solvent formation

| | |
|---|---|
| Solvents used | Dichloromethane (Weight of PCL/Volume of DCM: 0.05 g/ml-1 g/ml)/ Trichloromethane (Weight of PCL/Volume of TCM: 0.05 g/ml-1 g/ml) |
| Polymer added | 1 g of PCL |
| Metallic materials added | 0.1 g to 1 g magnesium beads |
| Sonication time | 30 mins to 1 hr |
| Drying duration | 12-24 hrs |
| Heat treatment temperature | 60° C.-80° C. |
| Heat treatment time | 30 mins to 3 hrs |

Note:
The ratio of the polymer to the metallic materials can be varied (e.g., 99.9% PCL/0.1% Mg to 50% PCL/50% Mg)

Example 7: Thermal Formation Method

Figure 2:
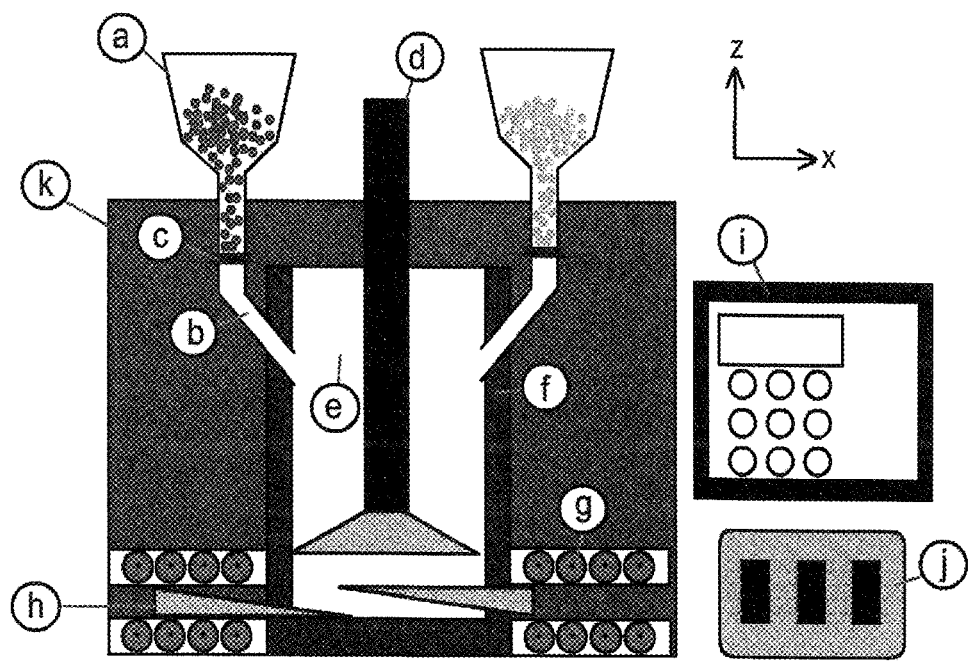
FIG. 2 shows a thermal-mechanical mixing machine that can be used in a fabrication method according to an embodiment of the subject invention.

The biodegradable polymer together with the surface-treated biodegradable metallic materials can undergo a thermal treatment in a thermal-mechanical mixing machine, as seen in FIG. 2. The biodegradable polymer(s) are mixed with surface-treated biodegradable metallic material(s) through a thermal-mechanical process. The thermal-mechanical process includes five main steps: melt polymer by thermal process; add metallic powder into melt polymer to form pre-hybrid material; shear pre-hybrid material in x and y axis; compress pre-hybrid material along the direction of z axis; and the shearing and compression steps are repeated until a hybrid material with evenly distributed components is achieved. The thermal-mechanical mixing device of FIG. 2 has been designed to carry out the thermal-mechanical process. The mixing device can be programmed to make a specific environment for fabricating different compositions of hybrid by adjusting a set of parameters.

The set of parameters includes: temperature; magnitude of applied mechanical force; direction of applied mechanical force; sequence of raw materials feed; timing of raw materials feed; and duration of each action. The parts of the mixing device of FIG. 2 are as follows: a) raw materials trays; b) raw materials transfer pipe; c) valve; d) vertical compressor; e) mixing chamber; f) heat element; g) support rollers; h) horizontal rolling plate; i) user input interface; j) controller; and k) outer most shell. Raw materials are stored in raw materials trays (a) and are ready to be fed into the mixing chamber (e). The raw materials trays (a) are connected to the mixing chamber (e) via the raw materials transfer pipes (b). The amount of raw materials to be fed is controlled by the valves (c) situated at the chamber side end of the raw materials transfer pipes (b). All surfaces (except that of the roller plates) which are in contact with raw/hybrid materials are coated with polytetrafluoroethylene (TEFLON) which is to avoid the sticky hybrid blocking the pipes, trays, and chamber. Surfaces of the horizontal rolling plates (h) are coated with reinforced glass that provides sufficient friction to shear the hybrid materials during rolling. The temperature of the mixing chamber is controlled by a heating system at the outer wall of the mixing chamber. The controller (j) controls all action according to the user pre-set program.

Example 8: 150 μm Magnesium Beads

Figure 3:
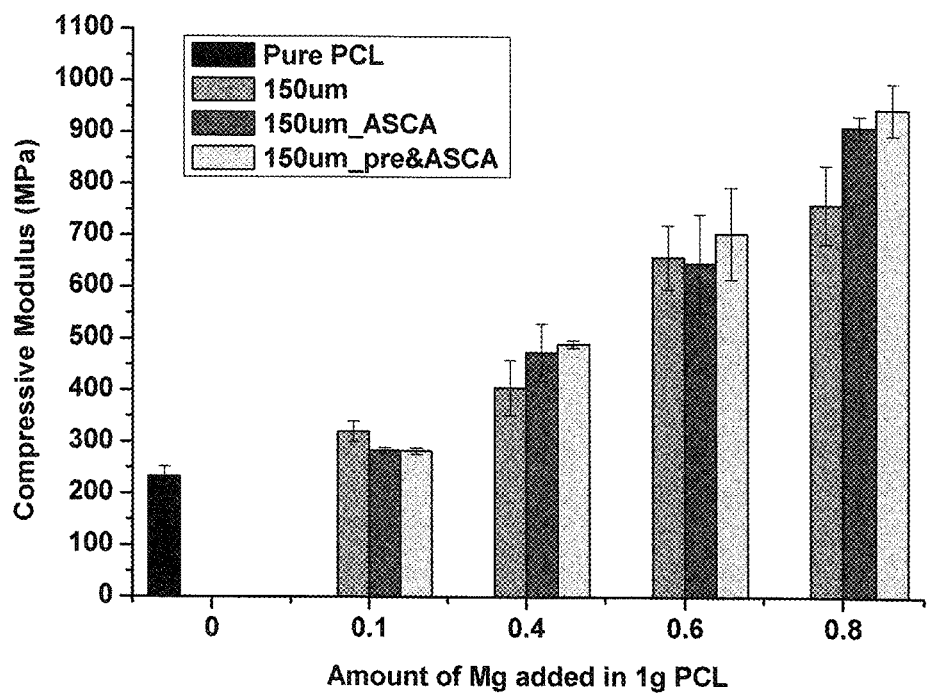
FIG. 3 shows compressive modulus as a function of amount of magnesium in a hybrid material according to an embodiment of the subject invention.
Figure 5:
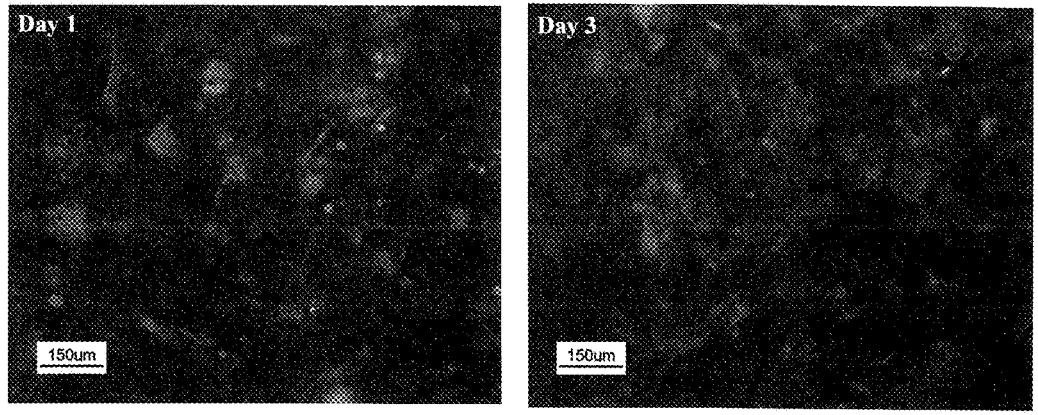
FIGS. 5 and 6 show fluorescent photos using enhanced Green Fluorescent Protein Osteoblasts (eGFPOB) culture.

Magnesium beads with a size of about 150 μm were used to fabricate an embodiment of the hybrid material of the subject invention. The polymer used was PCL. Tables 8 and 9 show the process conditions used. Table 8 is with no pre-heat treatment, and Table 9 is with pre-heat treatment. All values listed will work with slight variations, such that each value should be interpreted as having the word "about" in front of it. Additionally, FIG. 3 shows the compressive modulus for the resulting hybrid materials ("_ASCA" indicates no pre-heat treatment, and "_pre&ASCA" indicates pre-heat treatment; the amount of Mg is in grams). FIG. 5 shows fluorescent photos after 1 day and after 3 days using enhanced Green Fluorescent Protein Osteoblasts (eGFPOB) culture by incorporating 0.1 g ASCA-treated 150 μm magnesium beads as an example. The photos suggest that the hybrid material of the subject invention is compatible with the growth of osteoblasts.

TABLE 8

150 μm Magnesium beads with no pre-heat treatment

| | |
|---|---|
| Metallic material | 150 μm Magnesium beads (5 g) |
| Silane Treatment | |
| Silane coupling agent | 3-Aminoproyltrimethylsilane (Weight of Mg/Volume of ASCA: 2 g/ml) |
| Solvent | Cyclohexane (250 ml) |
| Catalyst | Triethylamine (0.75 ml) |
| Treatment Temperature | 80° C. |
| Treatment Time | 3 hrs |
| Post Heat Treatment | |
| Temperature | 80° C. |
| Duration | 5 hrs |
| Pressure | 100 mBar |
| Hybrid fabrication | |
| Amount of Mg beads added | 0.1 g; 0.4 g; 0.6 g; 0.8 g |
| Amount of PCL added | 1 g |
| Method of fabrication | Thermal formation method |

TABLE 9

150 μm Magnesium beads with pre-heat treatment

| | |
|---|---|
| Metallic material | 150 μm Magnesium beads (5 g) |
| Pre-treatment | |
| Temperature Duration | 80° C. 24 hrs |
| Silane Treatment | |
| Silane coupling agent | 3-Aminoproyltrimethylsilane (Weight of Mg/Volume of ASCA: 2 g/ml) |
| Solvent | Cyclohexane (250 ml) |
| Catalyst | Triethylamine (0.75 ml) |
| Treatment Temperature | 80° C. |
| Treatment Time | 3 hrs |
| Post Heat Treatment | |
| Temperature | 80° C. |
| Duration | 5 hrs |
| Pressure | 100 mBar |
| Hybrid fabrication | |
| Amount of Mg beads added | 0.1 g; 0.4 g; 0.6 g; 0.8 g |
| Amount of PCL added | 1 g |
| Method of fabrication | Thermal formation method |

Example 9: 45 μm Magnesium Beads

Figure 4:
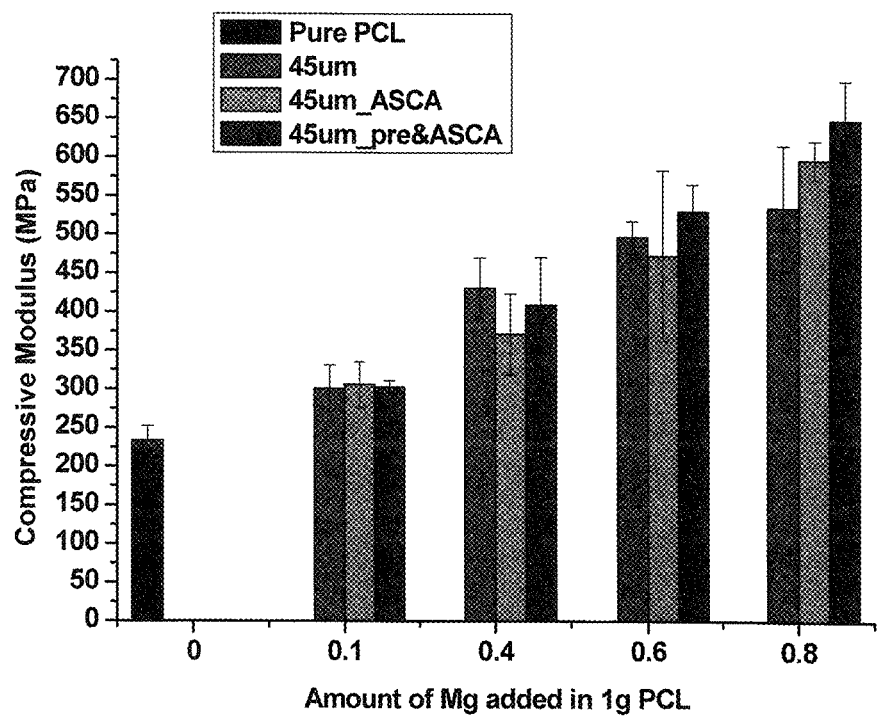
FIG. 4 shows compressive modulus as a function of amount of magnesium in a hybrid material according to an embodiment of the subject invention.
Figure 6:
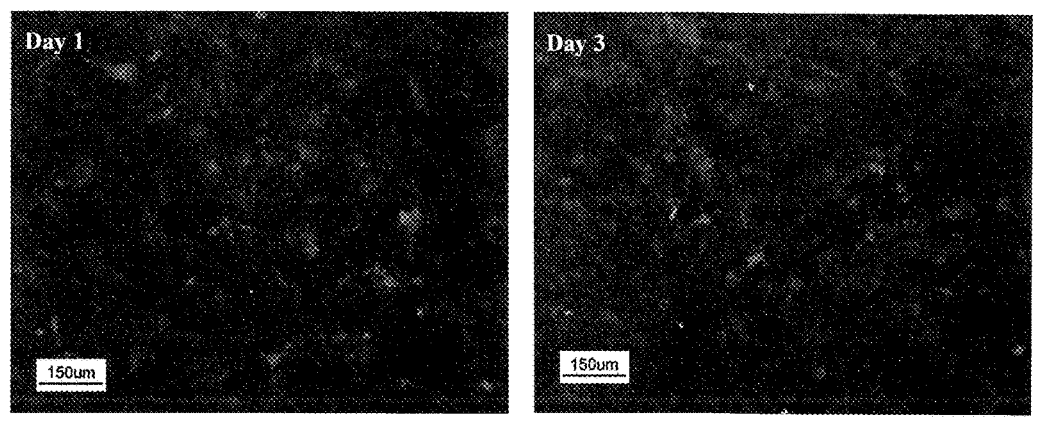

Magnesium beads with a size of about 45 μm were used to fabricate another embodiment of the hybrid material of the subject invention. The polymer used was PCL. Tables 10 and 11 show the process conditions used. Table 10 is with no pre-heat treatment, and Table 11 is with pre-heat treatment. All values listed will work with slight variations, such that each value should be interpreted as having the word "about" in front of it. Additionally, FIG. 4 shows the compressive modulus for the resulting hybrid materials ("_ASCA" indicates no pre-heat treatment, and "_pre&ASCA" indicates pre-heat treatment; the amount of Mg is in grams) FIG. 6 shows fluorescent photos after 1 day and after 3 days using enhanced eGFPOB culture by incorporating 0.1 g ASCA-treated 45 µm magnesium beads as an example. The photos suggest that the hybrid material of the subject invention is compatible with the growth of osteoblasts.

TABLE 10

45 µm Magnesium beads with no pre-heat treatment

| | |
|---|---|
| Metallic material | 45 µm Magnesium beads (5 g) |
| *Silane Treatment* | |
| Silane coupling agent | 3-Aminoproyltrimethylsilane (Weight of Mg/Volume of ASCA: 2 g/ml) |
| Solvent | Cyclohexane (250 ml) |
| Catalyst | Triethylamine (0.75 ml) |
| Treatment Temperature | 80° C. |
| Treatment Time | 3 hrs |
| *Post Heat Treatment* | |
| Temperature | 80° C. |
| Duration | 5 hrs |
| Pressure | 100 mBar |
| *Hybrid fabrication* | |
| Amount of Mg beads added | 0.1 g; 0.4 g; 0.6 g; 0.8 g |
| Amount of PCL added | 1 g |
| Method of fabrication | Thermal formation method |

TABLE 11

45 µm Magnesium beads with pre-heat treatment

| | |
|---|---|
| Metallic material | 45 µm Magnesium beads (5 g) |
| *Pre-treatment* | |
| Temperature Duration | 80° C. |
| | 24 hrs |
| *Silane Treatment* | |
| Silane coupling agent | 3-Aminoproyltrimethylsilane (Weight of Mg/Volume of ASCA: 2 g/ml) |
| Solvent | Cyclohexane (250 ml) |
| Catalyst | Triethylamine (0.75 ml) |
| Treatment Temperature | 80° C. |
| Treatment Time | 3 hrs |
| *Post Heat Treatment* | |
| Temperature | 80° C. |
| Duration | 5 hrs |
| Pressure | 100 mBar |
| *Hybrid fabrication* | |
| Amount of Mg beads added | 0.1 g; 0.4 g; 0.6 g; 0.8 g |
| Amount of PCL added | 1 g |
| Method of fabrication | Thermal formation method |

Compression testing was performed to measure the strength of hybrid materials of the subject invention.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A hybrid material, comprising:
    a biodegradable polymer;
    a biodegradable metallic material surface-treated by plasma immersion ion implantation or plasma immersion ion implantation and deposition; and
    a silane coupling agent chemically bonded to the surface-treated biodegradable metallic material and the biodegradable polymer,
    wherein the biodegradable polymer is a copolymer of ε-caprolactone (ε-CL) and γ-butyrolactone (γ-BL), δ-valerolactone (δ-VL), γ-valerolactone (γ-VL), γ-caprolactone (γ-CL), or any combination thereof.

2. The hybrid material according to claim 1, wherein the surface-treated biodegradable metallic material comprises magnesium, magnesium alloy, or both.

3. The hybrid material according to claim 1, wherein the surface-treated biodegradable metallic material comprises magnesium beads with a size of from about 100 nm to about 150 µm.

4. The hybrid material according to claim 1, wherein the silane coupling agent is 3-(trimethoxysilyl)propylmethacrylate or 3-aminopropyltrimethoxysilane.

5. A method of fabricating the hybrid material according to claim 1, wherein the method comprises:
    performing a surface treatment process on the biodegradable metallic material, wherein performing the surface treatment process on the biodegradable metallic material comprises performing a plasma immersion ion implantation process or a plasma immersion ion implantation and deposition process;
    dissolving the biodegradable polymer in an organic solvent to form a solution;
    adding the biodegradable metallic material, after the surface treatment process has been performed, to the solution;
    sonicating the solution;
    drying the solution to obtain a pre-hybrid material;
    performing a heat treatment process on the pre-hybrid material; and
    performing a coupling agent treatment on the surface-treated biodegradable metallic material before adding the biodegradable metallic material to the solution;
    wherein performing the coupling agent treatment comprises:
        adding the silane coupling agent and a catalyst to a second solvent to form a coupling agent solution;
        adding the biodegradable metallic material to the coupling agent solution to form a coupling agent solution mixture;
        heating the coupling agent solution mixture under reflux with nitrogen; and
        heat-treating the surface-treated biodegradable metallic material in a low-vacuum oven, and
    wherein the biodegradable polymer is a copolymer of ε-caprolactone (ε-CL) and γ-butyrolactone (γ-BL), δ-valerolactone (δ-VL), γ-valerolactone (γ-VL), γ-caprolactone (γ-CL), or any combination thereof.

6. The method according to claim 5, wherein the silane coupling agent is 3-(trimethoxysilyl)propylmethacrylate or 3-aminopropyltrimethoxysilane.

7. The method according to claim 6, wherein heating the coupling agent solution mixture comprises heating the coupling agent solution mixture at a temperature of from about 80° C. to about 110° C. for a period of time of about 3 hours;
wherein heat-treating the biodegradable metallic material comprises heat-treating the biodegradable metallic material at a temperature of about 80° C. to about 100° C. for a period of time of about 5 hours to about 8 hours at a pressure of about 100 mBar;
wherein the second solvent is cyclohexane or toluene; and
wherein the catalyst is propylamine or triethylamine.

8. The method according to claim 5, wherein the organic solvent is dichloromethane or trichloromethane;
wherein sonicating the solution comprises sonicating the solution for a period of time of from about 30 minutes to about 1 hour;
wherein drying the solution comprises drying the solution for a period of time of from about 12 hours to about 24 hours; and
wherein performing a heat treatment process on the pre-hybrid material comprises performing a heat treatment process on the pre-hybrid material at a temperature of about 80° C. for a period of time of from about 30 minutes to about 1 hour.

9. The method according to claim 5, wherein performing a surface treatment process on the biodegradable metallic material comprises performing the plasma immersion ion implantation process with a base pressure of about $7.0 \times 10^{-6}$ Torr, a working voltage of from about 15 kV to about 40 kV, a pulse width of about 30 μs, an implantation time of about 3 hours to about 4 hours, a frequency of about 200 Hz, and a working pressure of from about $5.0 \times 10^{-4}$ Torr to about $6.4 \times 10^{-4}$ Torr.

10. The method according to claim 5, wherein performing a surface treatment process on the surface-treated biodegradable metallic material comprises performing the plasma immersion ion implantation and deposition process utilizing:
a negative high voltage power supply with current of about 1.0 mA, a voltage with a magnitude of about 15 kV, a pulse duration of about 300 μs, and a frequency of about 10 Hz; and
a pulsed filtered cathodic arc source with an arc current of about 0.1 A, an arc voltage with a magnitude of about 92V, a triggering voltage with a magnitude of about 12.6 kV, a coil current of about 2.3 A, a pulse duration of about 250 μs, and a frequency of about 10 Hz.

11. A method of fabricating the hybrid material according to claim 1, wherein the method comprises:
performing a surface treatment process on the biodegradable metallic material, wherein performing the surface treatment process on the biodegradable metallic material comprises performing a plasma immersion ion implantation process or a plasma immersion ion implantation and deposition process;
melting the biodegradable polymer by a thermal process to obtain a polymer melt;
adding the biodegradable metallic material to the polymer melt to form a pre-hybrid material;
shearing the pre-hybrid material in a first direction and a second direction;
compressing the pre-hybrid material along a third direction to obtain the hybrid material; and
performing a coupling agent treatment on the biodegradable metallic material before adding the surface-treated biodegradable metallic material to the solution;
wherein performing the coupling agent treatment comprises:
adding the silane coupling agent and a catalyst to a second solvent to form a coupling agent solution;
adding the biodegradable metallic material to the coupling agent solution to form a coupling agent solution mixture;
heating the coupling agent solution mixture under reflux with nitrogen; and
heat-treating the surface-treated biodegradable metallic material in a low-vacuum oven, and
wherein the biodegradable polymer is a copolymer of ε-caprolactone (ε-CL) and γ-butyrolactone (γ-BL), δ-valerolactone (δ-VL), γ-valerolactone (γ-VL), γ-caprolactone (γ-CL), or any combination thereof.

12. The method according to claim 11, wherein the silane coupling agent is 3-(trimethoxysilyl)propylmethacrylate or 3-aminopropyltrimethoxysilane;
wherein heating the coupling agent solution mixture comprises heating the coupling agent solution mixture at a temperature of from about 80° C. to about 110° C. for a period of time of about 3 hours;
wherein heat-treating the biodegradable metallic material comprises heat-treating the biodegradable metallic material at a temperature of about 80° C. to about 100° C. for a period of time of about 5 hours to about 8 hours at a pressure of about 100 mBar;
wherein the second solvent is cyclohexane or toluene; and
wherein the catalyst is propylamine or triethylamine.

13. The method according to claim 11, wherein performing a surface treatment process on the biodegradable metallic material comprises performing the plasma immersion ion implantation and deposition process utilizing:
a negative high voltage power supply with current of about 1.0 mA, a voltage with a magnitude of about 15 kV, a pulse duration of about 300 μs, and a frequency of about 10 Hz; and
a pulsed filtered cathodic arc source with an arc current of about 0.1 A, an arc voltage with a magnitude of about 92V, a triggering voltage with a magnitude of about 12.6 kV, a coil current of about 2.3 A, a pulse duration of about 250 μs, and a frequency of about 10 Hz.

14. The method according to claim 11, wherein performing a surface treatment process on the biodegradable metallic material comprises performing the plasma immersion ion implantation process with a base pressure of about $7.0 \times 10^{-6}$ Torr, a working voltage of from about 15 kV to about 40 kV, a pulse width of about 30 an implantation time of about 3 hours to about 4 hours, a frequency of about 200 Hz, and a working pressure of from about $5.0 \times 10^{-4}$ Torr to about $6.4 \times 10^{-4}$ Torr.

15. The hybrid material according to claim 1, wherein the surface-treated biodegradable metallic material comprises magnesium, magnesium alloy, or both.

16. The hybrid material according to claim 1, wherein the surface-treated biodegradable metallic material comprises magnesium beads with a size of from about 100 nm to about 150 μm.

17. The hybrid material according to claim 1, wherein the silane coupling agent is 3-(trimethoxysilyl)propylmethacrylate or 3-aminopropyltrimethoxysilane.

18. The hybrid material according to claim 1, wherein the surface-treated biodegradable metallic material comprises magnesium beads with a size of from about 100 nm to about 150 μm.

* * * * *